United States Patent [19]

Dorai

[11] Patent Number: 5,180,857
[45] Date of Patent: Jan. 19, 1993

[54] REDUCTION OF MOLECULAR WEIGHT OF POLY(TETRAMETHYLENE ETHER) GLYCOL

[75] Inventor: Suriyanarayan Dorai, Lockport, N.Y.

[73] Assignee: E. I. Du Pont de Nemours and Company, Wilmington, Del.

[21] Appl. No.: 847,643

[22] Filed: Mar. 10, 1992

[51] Int. Cl.$^5$ ............................................... L07L 43/11
[52] U.S. Cl. ...................................... 568/617; 560/227
[58] Field of Search .......................... 568/617; 560/227

[56]  References Cited

U.S. PATENT DOCUMENTS 3,925,484  12/1975  Baker ............................. 260/615 B
4,120,903  10/1978  Pruckmayr et al. ............. 260/615 B
4,163,115   7/1979  Heinsohn et al. ................... 560/240

Primary Examiner—Howard T. Mars

[57]  ABSTRACT

A process for reducing the molecular weight of polytetramethylene ether glycol without significant conversion of polytetramethylene ether glycol to tetrahydrofuran monomer is disclosed. The process involves a two-step procedure. The first step comprises reacting polytetramethylene ether glycol with a perfluoroalkyl carboxylic acid to form a perfluoroalkyl ester of polytetramethylene ether glycol. That ester is, in the second step, converted back to polytetramethylene ether glycol of reduced molecular weight by hydrolysis or alcoholysis.

22 Claims, No Drawings

REDUCTION OF MOLECULAR WEIGHT OF POLY(TETRAMETHYLENE ETHER) GLYCOL

FIELD OF THE INVENTION

The present invention relates to a process for reducing the average molecular weight of poly(tetramethylene ether) glycol (PTMEG) by reaction with certain perfluorocarboxylic acids, particularly trifluoroacetic acid.

BACKGROUND OF THE INVENTION

PTMEG is a commodity in the chemical industry, used mainly in the manufacture of polyurethanes and polyesters. Functioning as a chain segment, PTMEG imparts resilience, flexibility, and softness to these materials. Generally, PTMEG is manufactured by way of cationic ring-opening polymerization of tetrahydrofuran (THF) in the presence of a suitable cationic initiator such as fluorosulfonic acid. Such polymerization of THF was first observed by Meerwein et al. in the late 1930's and is discussed in German Patent No. 741,476.

The molecular weight of PTMEG significantly influences the physical properties of both the PTMEG and the products derived from it. For example, PTMEG of relatively low molecular weight is a sticky, viscous oil at room temperature while, at higher molecular weights, it is thicker and more waxy. As is true of all polymeric compounds, the molecular weight of PTMEG may be expressed as either a "number-average" or a "weight-average". The number average molecular weight (Mn) is obtained by dividing the weight of a sample by the number of molecules of which it is composed. The weight-average molecular weight (Mw), on the other hand, is defined as the ratio of the sum of the mathematical products obtained by multiplying each molecular weight present in the sample by its corresponding fractional weight and the total sample weight. In practice, Mn and Mw are normally determined via such methods as gel permeation chromatography (GPC). Since a typical sample of PTMEG is composed of molecules of different degrees of polymerization, a distribution of molecular weights exists and as a result, values of Mn and Mw are not equivalent. The ratio Mw/Mn, referred to as the polydispersity, is indicative of the breadth of distribution of molecular weights for a given sample of polymer.

Although PTMEG may be produced with molecular weights in the millions, the most useful commercial varieties are those with number average molecular weights in the range between about 250 and 3500. The most common method of producing PTMEG with a Mn in this range is by polymerizing THF in the presence of fluorosulfonic acid (FSA). That method has several disadvantages however. For example, the FSA used in the polymerization cannot be recovered for reuse and the disposal of the toxic and corrosive spent acids, sulfuric acid and hydrofluoric acid, produced as a by-product present a serious environmental problem. In addition, the PTMEG product may contain some small but significant number of fluorine end groups.

More recently, processes for the manufacture of PTMEG have been developed which eliminate the FSA disposal problem. In U.S. Pat. No. 4,120,903, for example, Pruckmayr et al. describe a process in which PTMEG is produced by polymerizing THF using a polymeric catalyst which contains sulfonic acid groups. Representative of such catalysts is NAFION ® perfluorosulfonic acid resin, a product of E. I. du Pont de Nemours and Company. The Mn of the PTMEG produced according to that invention was about 10,000 in the example cited. On the other hand, Heinsohn et al. in U.S. Pat. No. 4,163,115, disclose a process for manufacturing esters of PTMEG through polymerization of THF in a medium containing an acylium ion precursor such as acetic anhydride, a polymeric catalyst which contains sulfonic acid groups, and optionally, a carboxylic acid such as acetic acid. Manipulating the ratio of carboxylic acid to acylium ion precursor affords enhanced control of molecular weight of the ester. According to that invention, ester end-capped PTMEG with Mn in the rang of 660 to 3,000 may be produced.

In instances where the molecular weight of the PTMEG produced by such processes is greater than that desired, it would be useful to have a process by which the molecular weight of PTMEG could be reduced to one within the acceptable range. In one such method (U.S. Pat. No. 3,925,484, M. C. Baker), high molecular weight PTMEG is treated with a strong sulfonic acid ion-exchange resin as catalyst to partially reverse the polymerization of THF, thereby converting some of the high molecular weight PTMEG to THF monomer and yielding PTMEG with a narrow molecular weight distribution. The number average molecular weight of the polymer tends to increase initially because of the high number of low molecular weight chains which are more easily depolymerized. If the duration of Baker's treatment were prolonged, depolymerization of the high molecular weight chains would take place to an increasing extent so that ultimately essentially all of the initial PTMEG would be converted to THF.

SUMMARY OF THE INVENTION

The present invention relates to a process for reducing the average molecular weight of PTMEG without significant conversion of PTMEG to THF. It is essentially a two-step procedure, the first of which comprises reacting PTMEG with a perfluoroalkyl carboxylic acid to form a perfluoroalkyl ester of PTMEG. That ester is, in the second step, converted back to PTMEG by hydrolysis or less preferably alcoholysis of the ester end groups. The PTMEG obtained as a product of the present invention is a lower number average molecular weight relative to the average molecular weight of the PTMEG used as starting material. In addition to low molecular weight PTMEG, the alcoholysis reaction produced an alkyl ester of the perfluorocarboxylic acid which can be separately converted by alcoholysis or hydrolysis so as to regenerate the perfluorocarboxylic acid required for the first step of the process.

DETAILED DESCRIPTION OF THE INVENTION

The two primary steps of the process of this invention can be represented by the chemical reactions described below. for the purpose of simplifying the description of the process given below, the high molecular weight PTMEG used as a starting material is designed "HMW PTMEG"; the lower molecular weight ester formed in the first step of the process is designated "LMW PTMEG Ester", and the PTMEG produced by the process is designated as "LMW PTMEG".

Reaction 1

In Reaction 1, the polymeric chain of HMW PTMEG is broken by the acid, forming a mixture of LMW mono- and di-perfluoroalkyl esters of PTMEG as shown: [Mono-ester is not shown]

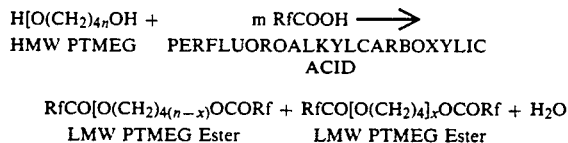

$$Rf CO[O(CH_2)_4]_{(n-x)} OCRf + Rf CO[O(CH_2)_4]_x OCRf + H_2O$$
LMW PTMEG Ester        LMW PTMEG Ester The two esters differ in their chain lengths. One of the LMW PTMEG esters has (n-x) oxytetramethylene repeat units while the other has X units. Actually, there can be more than two but it is important to satisfy the criteria that the sum of oxytetramethylene units from all these esters is equal to the oxytetramethylene units in the original PTMEG starting material, wherein:

Rf is a perfluoroalkyl group containing one to three carbon atoms;

n and x are the number of oxytetramethylene repeating units of the HMW PTMEG and LMW PTMEG ester molecules, respectively, the difference of which is the number of repeating units for the other LMW perfluoroalkyl ester molecule.

m is the number of perfluoroalkylcarboxylic acid molecules incorporated in the esterification of PTMEG, and also the number of moles of water formed.

In Reaction 1, the HMW PTMEG, perfluorocarboxylic acid, and water are brought together to form a reaction mass. Water is not necessary for the reaction. However, in a plant, it is possible to recycle either methyl trifluoroacetate or trifluoroacetic acid. If methyl trifluoroacetate is recycled, water is needed for the in situ hydrolysis. The most cost-effective way of recycling trifluoro acetic acid is to return this as trifluoroacetic acid/water azeotrope. The azeotrope is produced when hydrolyzing the ester. In either case, there is water in the reaction. Generally, the mixture is pressurized. However, pressure is not necessary and autogenous conditions will suffice during which the reaction medium is heated and then held for a designated period of time during which the reaction occurs. Following reaction, the mixture is allowed to cool, after which it is washed with water. Wash water and unreacted acid are then separated from the mixture, yielding the LMW PTMEG Ester which is converted to LMW PTMEG in Reaction 2 of the process.

The number-average molecular weight of the HMW PTMEG in Reaction 1 may range from 1000 to 25,000 and preferably from 1000 to 15,000, the most preferred being between 3000 and 10,000. The acid in Reaction 1 is a perfluoroalkylcarboxylic acid (RfA), such as trifluoroacetic acid (TFA), pentafluoropropionic acid, or heptafluorobutanoic acid, while the preferred reagent is TFA. Enough RfA should be added so that the weight ratio of RfA to PTMEG is 0.05 to 1.50 on a basis of 100% acid, the preferred ratio being in the range of 0.15 to 1.0. The most preferred weight ratio lies between 0.2 and 0.7. The mole ratio of the RfA will always be from at least 2 to 20 times greater than the starting number average molecular weight of the PTMEG, starting number average molecular weight of the PTMEG, and this ratio will depend greatly on the final number average molecular weight desired for the product PTMEG.

Basically, the bigger the reduction is molecular weight desired the more RfA is required.

The reaction mixture is heated to a temperature in the range of 100° to 250° C., preferably 120° C. to 200° C., while the most preferred mode calls for temperatures between 130° and 180° C. The pressure at which the reaction is conducted has not been found to significantly affect the results obtained. The actual pressure in the reactor will be the saturation pressure of the RfA at the given reaction temperature. Once the reactor contents have been heated and are under pressure, the mixture should be maintained at those conditions for a period of 0.1 to 8.0 hours and preferable from 0.5 to 4.0 hours. The most preferred duration of reaction is in the range of 0.5 to 3.0 hours.

Reaction 2

In Reaction 2, the LMW PTMEG Ester can be converted to LMW PTMEG by a process such as that described by Pruckmayr in U.S. Pat. No. 4,230,892. For example, the LMW PTMEG Ester can be converted to LMW PTMEG via an alcoholysis reaction in which the LMW PTMEG Ester is reacted with an alkanol having 1 to 3 carbon atoms in the presence of an ester exchange catalyst. Magnesium oxide is the preferred heterogeneous catalyst. Other suitable catalyst include CaO, NaOH and NaOMe. Methanol is the preferred alkanol. The alcoholysis reaction is preformed in absence of water and generates as a by-product the perfluoroalkyl ester of the acid used in Reaction 1. The Alcoholysis reaction does not function in the presence of water. It can be illustrated by the following equation:

LMW PTMEG Ester

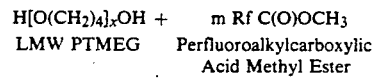

wherein:

Rf is a perfluoroalkyl group containing 1 to 3 carbon atoms;

x is the number of oxytetramethylene repeating units of the HMW perfluoroalkylester or LMW PTMEG molecules; m represents the amount of methanol required to achieve complete methanolysis of the product PTMEG.

The perfluoroalkyl methyl ester, product as a by-product in Reaction 2, can be converted by a staged equilibrium hydrolysis to RfA for use in Reaction 1 process. Although effective, such as hydrolysis adds to the expense of the process, because it adds another process step and requires additional equipment. An alternative to using a separate hydrolysis step to regenerate the acid is to use, in place of the acid in Reaction 1, a mixture of water and the perfluoroalkyl methyl ester produced in Reaction 2. Such mixture, when added to Reaction 1, will generate, in situ, the perfluorocarboxylic acid necessary for reaction. By this method, the perfluoroalkyl ester generated by the alcoholysis reaction can be combined with water and used again in Reaction 1. This is the most cost effective way of generating perfluorocarboxylic acid for Reaction 1.

The LMW PTMEG obtained as a product of the process of this invention has a number-average molecular weight between 250 and 3500. The preferred Mn is in the range of 650 to 2900 and the most preferred is between 650 and 2100.

The preferred mode of practicing this invention entails the use of trifluoroacetic acid (TFA) as the reagent for reducing molecular weight. Methanol is used in the alcoholysis reaction producing LMW PTMEG and methyl trifluoroacetate (MTFA). TFA, may be used as such in Reaction 1, or it may be regenerated from the MTFA either by recycling the MTFA directly to Reaction 1 and allowing the TFA to form in situ or by a separate staged hydrolysis process. Where MTFA is used as the in situ source of TFA, an excess of MTFA of 4 to 60, preferably 4 to 12 times that of the HMW PTMEG starting material on a molar basis is required depending on the final number average molecular weight desired.

To practice the alcoholysis aspect of the invention, a mixture of poly(tetramethylene ether) diester starting material, catalyst and alkanol is first prepared. This can be done by simply mixing the three components together in a reactor, in any order. Preferably the catalyst is first slurried in the alkanol and this slurry is mixed with a solution of diester in alkanol. It is also important that all the three components are as dry as possible. Presence of water makes the catalyst alkaline and consequently could partially neutralize the diester. This decreases the recovery of the trifluoroacetic acid ester which is extremely expensive, and for this reason the presence of water is undesirable.

The mixture is prepared so that it contains about 5-80%, preferably 20-60% (by total weight of the diester and alkanol) of diester. The catalyst is present in the mixture at a concentration of 0.02-3%, preferably 0.1-0.5% by weight of the diester, which is substantially less than the stoichiometric quantities.

The catalyst used in this mixture is an oxide, hydroxide or alkoxide (in which the alkyl group contains 1-4 carbon atoms) of magnesium, calcium, sodium, barium or strontium. Sodium methoxide also is effective. The preferred catalyst is magnesium oxide because this particular catalyst leaves behind very little residue in the PTMEG.

The alkanol in the mixture is one containing 1-4 carbon atoms. Methanol is the preferred alcohol in all the cases.

It is also important that the polymeric diester (PTMETA) starting material be neutral or nearly neutral i.e. have a pH value of about 7 before catalyst is added, for if the pH value is below about 7, the effect on the alcoholysis reaction will be impeded. The pH of the diester can be brought to neutral value or near neutral value by vacuum distilling the diester of PTMEG.

The alcoholysis reaction mixture is then brought to its boiling point and held there, with stirring, while vapors of the alkyl trifluoroacetate which form, are continuously withdrawn from the reaction zone. In the usual case the boiling point of the mixture will be in the range of about 40°-150° C. If a temperature higher than this is required, the reaction can be run under a pressure of up to 100 atmospheres. The boiling and withdrawal of the alkyl trifluoroacetate is continued until the alcoholysis is substantially complete, i.e., until no more alkyl trifluoroacetate is detected in the vapor leaving the reaction vessel, as determined by gas chromatography.

The process can be conducted batch wise or in a continuous fashion. The continuous mode is preferred for its efficiency.

Although the process can be run in a single stage, it is preferably run in two or more stages, especially when run continuously, because this will give a higher degree of conversion. The continuous multi-stage process is run exactly as the one-stage process except that the contents of the first reactor are transferred sequentially to the others where alcoholysis is completed. Retention time in each reactor can be between 50 and 150 minutes. It may also be desirable to add the alkanol continuously to the secondary reactors in an amount equal to the amount of alkanol in the alkanol/alkyl trifluoroacetate withdrawn from the first reactor.

After the alcoholysis is completed, the catalyst and such other insoluble materials as may be present are removed from the reaction mass by conventional techniques such as filtration, decantation or centrifugation. Ordinarily and preferably, the catalyst is filtered from the reaction mass and recycled to one of the reactors, but the reaction mass also can be withdrawn from the reactor through a filter which holds back the catalyst and other insoluble and keeps them in the reactor.

The preferred catalyst is magnesium oxide or the hydroxide. The primary reason for this is that the magnesium salt of trifluoroacetic acid is practically insoluble in PTMEG and therefore the finished product PTMEG is virtually free of the magnesium radical. In contrast, the calcium salt of trifluoroacetic acid is soluble in PTMEG and therefore a substantial portion of the calcium salt is left behind in the product. If calcium oxide or hydroxide was used as the catalyst, the PTMEG product has to be washed with water to make it calcium-free. This is an additional step in the unit operation which is not preferred.

It also may be desirable, before or after the separation of the catalyst, to strip the reaction mass of residual alkanol and alkyl trifluoroacetate byproduct. This can be done by conventional engineering techniques.

The PTMEG product of this process can be put to any conventional use such as the preparation of polyester of polyurethanes.

The invention may be best illustrated by the following examples which are given by way of illustration; they are not intended to limit the scope of the invention.

EXAMPLE 1

This example demonstrates the use of TFA in reducing the molecular weight of PTMEG. A mixture, containing 20 grams (0.175 gm. mol) of trifluoroacetic acid, 30 grams of water, and 50 grams (0.0244 gm. mol) of PTMEG with a number-average molecular weight of 2048, is placed in a pressure-bomb. At room temperature, nitrogen is sparged through the dip tube for about 15 minutes to displace any dissolved oxygen present in the mixture. The bomb is closed, and the vapor phase was pressurized to 30 psig (207 kPa) with nitrogen. The contents of the bomb are heated to 153° C. throughout a period of 15 minutes, after which the pressure in the bomb is 125 psig (862 kPa). After the contents of the bomb are maintained at 153° C. for 2 hours, they are cooled to 45° C. within less than 5 minutes. The mixture is then washed with water which, along with the unreacted acid, is removed by distillation at 125° C., using sparged nitrogen to facilitate the separation. Approximately 52.1 grams of the bis-trifluoroacetate of PTMEG are recovered. The bis-trifluoroacetate of PTMEG is converted to PTMEG by hydrolysis. Thus, 20 grams (0.0144 mol) of the ester is mixed with 100 grams (5.56 mols) of water, and the mixture is heated to 155° C. in a manner similar to the MW reduction procedure. The material is cooled and the light phase containing about 17 grams of PTMEG was dried at 125° C. with sparged nitrogen. The number average molecular weight of the hydrolyzed material is 1180 as determined by gel permeation chromatography.

EXAMPLE 2

This example reports the use of MTFA used in situ as a source of TFA for the reduction of molecular weight of PTMEG. A mixture, containing 49.48 grams (0.387 mol) of methyl trifluoroacetate, 26.43 grams (1.468 mol) of water, and 44.9 grams (0.0067 gm. mol) of PTMEG with a number-average molecular weight of 6750 is placed in a pressure bomb and heated to 155° C. over 1.5 hours during which the pressure in the bomb reached 150 psig (1034 kPa). After the contents of the bomb are cooled, volatile components including methyl trifluoroacetate, trifluoroacetic acid, and methanol are stripped from the mixture. Approximately 52.1 grams of the bis-trifluoroacetate of PTMEG is recovered. This material was hydrolyzed as in Example 1 to yield 42.3 g of PTMEG with a number average molecular weight of 1028.

EXAMPLE 3 TO 6

Examples 3 through 6 are conducted in the same manner as that used in Example 2. Pertinent data and results are reported below. Data from Example 2 are included for comparison.

TABLE 1

Experimental Data for Examples 3-6

| Ex. | PTMEG Grams | MTFA Grams | H₂O Grams | Hold Temp. °C. | Max. Press. PSIG | Time Hours |
|-----|-------------|------------|-----------|----------------|------------------|------------|
| 3 | 70.1 | 44.9 | 71.3 | 155 | 135 | 2 |
| 4 | 50.2 | 20.2 | 30.2 | 155 | 125 | 2 |
| 5 | 50.7 | 41.1 | 33.8 | 155 | 135 | 2 |
| 6 | 51.0 | 30.7 | 20.0 | 155 | 135 | 2 |

| Example | Initial Mn PTMEG | Final Mn PTMEG |
|---------|------------------|----------------|
| 3 | 1982 | 1504 |
| 4 | 2072 | 1547 |
| 5 | 2072 | 1111 |
| 6 | 2072 | 1548 |

EXAMPLE 7

A 30 grams sample of PTMETA (number average molecular weight of 1010) is dissolved in 90.7 grams of methanol. After addition of 0.03 gram of magnesium oxide, the mixture is heated to 65° C. for about 4 hours. Only 0.418 gram of methyl trifluoroacetate is recovered which corresponds to only 8% of alcoholysis.

To the reaction mixture another 0.03 gram of MgO and 9.9 grams of methanol are added. (It was estimated that ~9.9 grams of methanol were lost and that increased amount of catalyst would improve the alcoholysis reaction.) The mixture is then heated to 65° C. for about 3.6 hours during which period an additional 4.65 grams of methyl trifluoroacetate is collected. The total amount of methyl trifluoroacetate collected corresponded to 99.3% of the bound trifluoroacetic acid present in the diester starting material.

The product is then dried for 1 hours at 100° C. in a vacuum of 1 mm mercury. Filter aid is added and the product is filtered to remove insoluable material. The resulting PTMEG product (number average molecular weight of 855) contained less than 1 ppm magnesium as determined by atomic absorption.

EXAMPLE 8

A 30 gram of the diester of PTMEG (number average molecular weight of 1140) is dissolved in 60 grams of methanol. After addition of 1 gram of MgO, the mixture is heated to 65° C. for about 3 hours with stirring while vapors from the reaction pot are condensed in a refrigerant-cooled glass vessel.

The product is then dried at 120° C. and under vacuum. Filter aid, 0.3 gram is added and the product is filtered to remove insoluble material. The resulting PTMEG material (number average molecular weight of 991) is found to be virtually free of carbonyl esters as indicted by an infrared spectroscopic analysis.

EXAMPLE 9

A 30 gram diester of PTMEG is dissolved in 70 grams of methanol. After the addition of 1 gram of calcium oxide, the mixture is heated to about 65° C. for about 3 hours with stirring while vapors from the reaction flask are condensed in a refrigerant-cooled glass vessel. The methyl trifluoroacetate collected corresponded to a conversion of 97%.

The product is then dried at 120° C. under vacuum. Filter aid, 0.3 gram are added and the product filtered to remove insoluble material. The clear transparent PTMEG contains about 1.9% as, the calcium content was analyzed to be in excess of 10,000 ppm. The PTMEG had an orange color which comes from dissolved calcium trifluoroacetate.

I claim:

1. A process for preparing poly(tetramethylene ether) glycols having reduced molecular weights, without significant conversion of said poly(tetramethylene ether) glycols to tetrahydrofuran, comprising:
   (a) reacting, as a starting material, a poly(tetramethylene ether) glycol having a number average molecular weight in the range between about 1000 and 25000 with a perfluorocarboxylic acid and an alkanol containing 1 to 3 carbon atoms, at a temperature of 100° C. to 250° C. for a reaction time of 0.1 to 8.0 hours under autogenous pressure to form a poly(tetramethylene ether) glycol ester said having a molecular weight lower than that of said poly(tetramethylene ether) glycol starting materials;
   (b) converting said lower molecular weight ester having a pH value of about 7 to a poly(tetramethylene ether) glycol by reaction with an alcohol or water; and
   (c) recovering from the reaction mixture a poly(tetramethylene ether) glycol having a number average molecular weight in the range between about 250 and 3500.

2. The process of claim 1 wherein said poly(tetramethylene ether) glycol starting material has a number average molecular weight between 1000 and 15,000.

3. The process of claim 1 wherein said poly(tetramethylene ether) glycol starting material has a number average molecular weight between 3000 and 10,000.

4. The process of claim 1 wherein said perfluorocarboxylic acid is trifluoroacetic acid.

5. The process of claim 1 wherein the weight ratio of said perfluorocarboxylic acid to poly(tetramethylene ether) glycol starting material is 0.05 to 1.50.

6. The process of claim 5 wherein said weight ratio is 0.15 to 1.0.

7. The process of claim 5 wherein said weight ratio is 0.2 to 0.7.

8. The process of claim 1 wherein said reaction temperature is 120° to 200° C.

9. The process of claim 1 wherein said reaction temperature is 130° to 180° C.

10. The process of claim 1 wherein said reaction time is 0.5 to 4.0 hours.

11. The process of claim 1 wherein said reaction time is 0.5 to 3.0 hours.

12. A process for preparing poly(tetramethylene ether) glycols having reduced molecular weights, without significant conversion of said poly(tetramethylene ether) glycols to tetrahydrofuran, comprising:
   (a) reacting, as a starting material, a poly(tetramethylene ether) glycol having a number average molecular weight in the range between about 1000 and 25000 and an ester of an alkanol containing 1 to 3 carbon atoms and a perfluorocarboxylic acid containing 2 to 4 carbon atoms, in the presence of water at a temperature of 100° to 250° C., and for a reaction time of 0.1 to 8.0 hours under autogenous pressure to provide a bis-perfluoroalkylcarboxylic ester of a lower molecular weight PTMEG;
   (b) separating said lower molecular weight PTMEG ester from the mixture of volatile components, including alcohol, perfluoroalkylcarboxylic ester and perfluoroalkylcarboxylic acid;
   (c) subjecting said lower molecular weight PTMEG ester having a pH value of about 7 to ester exchange with an alkanol containing 1 to 3 carbon atoms at a temperature of 55° to 175° C. for 1 to 8 hours; and
   (d) recovering a poly(tetramethylene ether) glycol having a number average molecular weight in the range between about 250 and 3500.

13. The process of claim 12 wherein said poly(tetramethylene ether) glycol starting material has a number average weight between 1000 and 15,000.

14. The process of claim 12 wherein said poly(tetramethylene ether) glycol starting material has a number average molecular weight between 3000 and 10,000.

15. The process of claim 12 wherein said perfluorocarboxylic acid is trifluoroacetic acid.

16. The process of claim 12 wherein the weight ratio of said perfluorocarboxylic acid to poly(tetramethylene ether) glycol starting material is 0.05 to 1.50.

17. The process of claim 16 wherein said weight ratio is 0.15 to 1.0.

18. The process of claim 16 wherein said weight ratio is 0.2 to 0.7.

19. The process of claim 12 wherein said reaction temperature is 120° C. to 200° C.

20. The process of claim 12 wherein said reaction temperature is 130° C. to 180° C.

21. The process of claim 12 wherein said reaction time is 0.5 to 4.0 hours.

22. The process of claim 12 wherein said reaction time is 0.5 to 3.0 hours.

* * * * *